(12) United States Patent
Arthur et al.

(10) Patent No.: US 9,247,980 B2
(45) Date of Patent: Feb. 2, 2016

(54) DEVICE FOR PERFORMING A SURGICAL PROCEDURE AND METHOD

(71) Applicant: KYPHON SARL, Neuchatel (CH)

(72) Inventors: Amy L. Arthur, Mountain View, CA (US); Mojan Goshayeshgar, Atherton, CA (US)

(73) Assignee: KYPHON SARL, Neuchatel (CH)

( * ) Notice: Subject to any disclaimer, the term of this patent is extended or adjusted under 35 U.S.C. 154(b) by 317 days.

(21) Appl. No.: 13/798,804

(22) Filed: Mar. 13, 2013

(65) Prior Publication Data

US 2014/0276875 A1 Sep. 18, 2014

(51) Int. Cl.
*A61B 17/88* (2006.01)

(52) U.S. Cl.
CPC ......... *A61B 17/8855* (2013.01); *A61B 17/8805* (2013.01); *A61B 17/8819* (2013.01)

(58) Field of Classification Search
CPC ........................ A61B 17/0483; A61B 17/8805
See application file for complete search history.

(56) References Cited

U.S. PATENT DOCUMENTS

| 5,054,497 | A | * | 10/1991 | Kapp et al. ................... 600/561 |
| 5,405,330 | A | | 4/1995 | Zunitch et al. |
| 5,681,325 | A | | 10/1997 | Hasson |
| 5,810,712 | A | | 9/1998 | Dunn |
| 5,865,817 | A | | 2/1999 | Moenning et al. |
| 6,039,725 | A | | 3/2000 | Moenning et al. |
| 6,110,182 | A | * | 8/2000 | Mowlai-Ashtiani .......... 606/130 |
| 6,287,281 | B1 | | 9/2001 | Nishtala et al. |
| 6,328,748 | B1 | * | 12/2001 | Hennig ........................ 606/130 |
| 6,488,664 | B1 | | 12/2002 | Solomon et al. |
| 7,637,915 | B2 | * | 12/2009 | Parmer et al. ................. 606/108 |
| 7,695,480 | B2 | * | 4/2010 | Solar et al. ................... 606/130 |
| 7,704,260 | B2 | * | 4/2010 | Skakoon et al. .............. 606/130 |
| 8,556,801 | B2 | * | 10/2013 | Liu ............................... 600/114 |
| 8,747,418 | B2 | * | 6/2014 | Qureshi et al. ............... 606/130 |
| 8,961,548 | B2 | * | 2/2015 | Buser et al. .................. 606/174 |
| 2003/0055436 | A1 | * | 3/2003 | Daum et al. .................. 606/130 |
| 2008/0077142 | A1 | * | 3/2008 | James et al. .................... 606/69 |
| 2008/0183191 | A1 | * | 7/2008 | Schoepp ....................... 606/130 |

* cited by examiner

*Primary Examiner* — David Bates
(74) *Attorney, Agent, or Firm* — Sorell Lenna & Schmidt LLP (57) ABSTRACT

A device includes a first member extending along an axis. The first member includes a first portion connected to a second portion by a hinge. Inner surface of the first and second portions define a cavity having a pivoting member is movably disposed therein. The pivoting member includes an inner surface defining a passageway having a second member disposed therein. A cap has an inner surface that engages an outer surface of the pivoting member. The pivoting member is movable between a first orientation such that the second portion is spaced apart from the pivoting member and the pivoting member is rotatable to a selected trajectory relative to the longitudinal axis and a second orientation such that the second portion engages the pivoting member to fix the second member in the selected trajectory. Methods of use are disclosed.

17 Claims, 4 Drawing Sheets

DEVICE FOR PERFORMING A SURGICAL PROCEDURE AND METHOD

TECHNICAL FIELD

The present disclosure generally relates to medical devices for the treatment of musculoskeletal structures, and more particularly to a surgical system and method that include a device configured to hold a surgical instrument while a surgical procedure is performed.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal bone which diminishes associated back pain.

Kyphoplasty procedures may also be used to treat fractures in other areas of a patient's body, such as, for example, a distal radius of the patient. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, screws and/or plates for fracture fixation.

In conventional kyphoplasty procedures, the IBT is inserted adjacent the bone defect by inserting the IBT through a cannula. An inflatable member of the IBT is expanded to create a void in or adjacent the bone defect. After the IBT creates the void, the IBT is removed from the cannula and a bone void filler is delivered through the cannula to the void in order to at least partially fill the void. It is therefore important that the cannula be properly oriented with respect to the bone defect. In conventional kyphoplasty procedures, the cannula is held at a desired trajectory by a physician or physician's assistant, so that the IBT or bone void filler may be delivered through the cannula to a location adjacent the bone defect or void created by the IBT.

Percutaneous delivery of IBT or bone filler material through the cannula to a bone defect or bone void can be difficult. For example, the IBT or bone void filler material may get stuck in the cannula. Furthermore, the distal end of the cannula must be positioned adjacent to the bone defect or bone void to allow the IBT or bone void filler to be delivered through the cannula to the bone defect or bone void. There is often little soft tissue and/or bony anatomy to hold the cannula in a stable position during delivery of the IBT or bone filler material. To stabilize the cannula, a surgical assistant is often required to provide an extra pair of hands to hold the cannula while a surgeon delivers the IBT or the bone filler material to the bone defect or bone void through the cannula. The present disclosure provides a device that acts as a second pair of hands to hold the cannula at a fixed trajectory to ensure that the cannula is properly positioned relative to the bone defect or bone void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device includes a first member extending along a longitudinal axis between a first end and a second end. The first end includes a first portion connected to a second portion by a hinge. An inner surface of the first portion and an inner surface of the second portion define a cavity. A pivoting member is movably disposed in the cavity and includes an inner surface defining a passageway. The pivoting member further includes a first end comprising a ball and a second end comprising a collet. A cap having an inner surface engages an outer surface of the collet. A second member disposed within the passageway. The pivoting member is movable between a first orientation such that the second portion is spaced apart from the pivoting member and the pivoting member is rotatable to a selected trajectory relative to the longitudinal axis and a second orientation such that the second portion engages the pivoting member to fix the second member in the selected trajectory.

In one embodiment, in accordance with the principles of the present disclosure, the surgical system includes a device comprising a first member extending along a longitudinal axis between a first end and a second end. The first end comprises an inner surface defining a substantially spherical cavity having silicone disposed about at least a portion thereof. The first end of the first member includes a first portion connected to a second portion of the first end by a hinge. The first and second portions are separated by a gap extending transverse to the longitudinal axis. A pivoting member is movably disposed in the cavity. The pivoting member includes an inner surface defining a passageway. A first end of the pivoting member comprises a ball and a second end of the pivoting member comprises a collet. The collet has a threaded outer surface. A second member is disposed within the passageway. The second member includes an inner surface defining a second passageway having an inflatable bone tamp, a bone void filler, a tool configured to deliver a bone void filler or a working cannula disposed therein. A cap has a threaded inner surface that engages the threaded outer surface of the collet. The cap is movable between a first orientation such that the threaded inner surface of the cap is spaced apart from the threaded outer surface of the collet and the second member is movably disposed within the passageway and a second orientation such that the threaded inner surface of the cap engages the threaded outer surface of the collet and the second member is fixed within the passageway. The first end of the first member includes a first portion having an opening and a second portion including a resilient tab configured for disposal in the opening to fix the first portion with the second portion. The pivoting member is movable between a first orientation such that the tab is spaced apart from the opening and the second member is rotatable to a selected trajectory relative to the longitudinal axis and a second orientation such that the tab is disposed in the opening to fix the second member in the selected trajectory.

In one embodiment, in accordance with the principles of the present disclosure, a method for repairing a bone is provided. The method comprises the steps of: providing a device comprising: a first member extending along a longitudinal axis between a first end and a second end, the first end comprising a first portion connected to a second portion of the first end by a hinge, an inner surface of the first portion and an inner surface of the second portion defining a cavity, the first portion having an opening and the second portion having a tab configured for disposal in the opening to fix the first portion with the second portion, a pivoting member movably disposed in the cavity, the pivoting member including an inner surface defining a passageway, a first end of the pivoting member comprising a ball and a second end of the pivoting member comprising a collet, the collet having a threaded outer surface, a cap having a threaded inner surface configured to engage the threaded outer surface of the collet; creating an access path to a defect in a bone; inserting the second end of the first member through the access path; inserting a second member into the passageway; moving the cap relative to the collet such that the threaded inner surface of the cap engages the threaded outer surface of the collet and the second member is fixed within the passageway; rotating the pivoting member to a selected trajectory relative to the longitudinal axis such that a distal end of the second member is positioned adjacent the bone defect; and moving the first portion relative to the second portion such that the tab is disposed in the opening to fix the second member in the selected trajectory.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method include a device configured to hold a surgical instrument while performing a surgical procedure to treat a bone defect, such as, for example a fracture.

In one embodiment, the system and method include a device configured to hold a cannula having a ball and socket configuration. The ball is configured to interface with a socket in a tail of the device. The ball includes a collet having a threaded outer surface. The ball and collet have an inner surface defining a passageway configured for disposal of a surgical tool, such as, for example, a cannula. A cap has a threaded inner surface configured to engage the threaded outer surface of the collet. As the threaded inner surface of the cap engages the threaded outer surface of the collet, the inner surface of the collet engages an outer surface of the collet to fix the cannula relative to the collet. That is, the cap tightens around the collet to rigidly hold the cannula. The tail has a first portion and a second portion connected to the first portion by a hinge. In some embodiments, the hinge is a living hinge. An inner surface of the first portion and an inner surface of the second portion define the socket. In some embodiments, the socket is lined with a deformable material, such as, for example, silicone to enhance engagement of the inner surfaces of the first and second portions with the ball. In one embodiment, a silicone lining can be used to hold the cannula in the ball.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bone disorders, such as, for example fractures in the anatomy of a patient, such as, for example, spinal bones or arm bones. It should be understood that the present principles are applicable to any bone structures, including but not limited to bones of the spine, arms, legs, feet, hands, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the arm, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for holding a surgical instrument while a surgical procedure is performed. The disclosure also includes a description of related methods of employing the disclosed surgical system. Alternate embodiments are also disclosed. Reference will now be made in detail to the exemplary embodiments of the present disclosure, which are illustrated in the accompanying figures. Turning now to FIGS. 1-5, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to treat a bone defect, such as, for example a fracture. System 30 includes a tail, such as, for example, a first member 32 extending along a longitudinal axis A between a first end 34 and a second end 36. End 34 includes an inner surface 38 defining a substantially spherical cavity 34 extending transverse to axis A configured for movable disposal of a substantially spherical portion of a component, such as, for example, a pivoting member 42. It is envisioned that all or only a portion of cavity 40 may be variously configured and dimensioned, such as, for example, planar, concave, convex, hemispherical, polygonal, irregular, uniform, non-uniform, staggered, tapered, consistent or variable, depending on the requirements of a particular application. It is further envisioned that cavity 40 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application. In some embodiments, cavity 40 includes a material 44, such as, for example, a deformable material such as, for example, silicone or silicone rubber disposed about at least a portion of surface 38 configured to enhance engagement between an outer surface of member 42 and member 32.

End 34 includes a first portion 46 connected to a second portion 48 of end 34 by a hinge, such as, for example, a living hinge 50. Portions 46, 48 are separated by a gap 49 extending transverse to axis A. Surface 38 defines a first hemispherical chamber 52 in portion 46 and a second hemispherical chamber 54 in portion 48. Chambers 52, 54 define cavity 40 when portion 46 is fixed with portion 48, as will be discussed. Hinge 50 allows portion 48 to rotate about portion 46 in the direction shown by arrow B or the direction shown by arrow BB such that portion 50 can close around member 42 to maintain member 42 in cavity 40. It is envisioned that all or only a portion of chamber 52 and/or chamber 54 may be variously configured and dimensioned, such as, for example, planar, concave, convex, hemispherical, spherical, polygonal, irregular, uniform, non-uniform, staggered, tapered, consistent or variable, depending on the requirements of a particular application. It is further envisioned that gap 49 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application.

In some embodiments, hinge 50 may include a barrel hinge, pivot hinge, butt/mortise hinge, case hinge, continuous hinge or piano hinge, concealed hinge, butterfly hinge or Parliament (UK) hinge, flag hinge, strap hinge, H hinge, HL hinge, counterflap hinge, flush hinge, coach hinge, rising butt hinge, double action spring hinge, tee hinge, friction hinge, security hinge, cranked hinge or stormproof hinge, lift-off hinge or self-closing hinge. In some embodiments, portions 46, 48 and hinge 50 are made from the same material, the material having a reduced thickness at hinge 50 to facilitate bending. In some embodiments, portions 46, 48 are made from the same material and hinge 50 comprises a material that is different from a material that portions 46, 48 are made from. In some embodiments, hinge 50 comprises a plurality of hinges that are each spaced apart from one another.

Portion 46 includes a first flange 56 extending perpendicular to axis A. Flange 56 includes a tab 58 extending therefrom in a direction that is parallel to axis A configured for disposal in a square or rectangular opening 60 extending in parallel to axis A through a second flange 62 extending perpendicular to axis A. Tab 58 is disposed in opening 60 defined by an inner surface of flange 62 to fix portion 46 with portion 48 such that member 42 is maintained in cavity 40. It is envisioned that flange 56, flange 62, tab 58 and/or opening 60 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application. It is further envisioned that all or only a portion of opening 60 may be variously configured and dimensioned, such as, for example, circular, oval, oblong, triangular, polygonal, irregular, uniform, non-uniform, offset, staggered, tapered, consistent or variable, depending on the requirements of a particular application.

Tab 58 includes a distal portion or arm 64 having a uniform width or diameter and a proximal portion including a catch 68 having a width or diameter that is greater than that of arm 64. Catch 66 extends in a direction that is perpendicular to axis A. Catch 66 includes a tapered upper surface 68 and a planar lower surface 70. Surface 68 extends at an acute angle relative to axis A and surface 70 extends perpendicular to axis A. To engage tab 58 with opening 60, tab 58 is positioned adjacent to opening 60 such that surface 68 engages the inner surface of flange 62 that defines opening 60. Tab 58 is then translated in a direction shown by arrow C such that catch 66 moves through opening 60 and surface 70 engages a distal surface of flange 62. In some embodiments, tab 58 is resiliently biased such that arm 64 engages the inner surface of flange 62 that defines opening 60 when surface 70 engages the distal surface of flange 62. It is envisioned that surface 68 and/or surface 70 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application.

Member 42 includes an inner surface 72 defining a passageway 74 having a cylindrical cross sectional configuration. A first end of member 42 includes a substantially spherical ball 76 and a second end of member 42 includes a collet 78 extending from ball 76. Passageway 74 extends through ball 76 and collet 78. Collet 78 includes a threaded outer surface 80 configured to engage a threaded inner surface 82 of a nut, such as, for example, cap 84 to engage cap 84 with collet 78 and fix a tool, such as, for example, a cannula 86 within passageway 74. Cannula 86 has an inner surface 88 defining a second passageway 90 having a cylindrical cross sectional configuration adapted for disposal of an inflatable bone tamp, a bone void filler and/or a tool configured to deliver a bone void filler therein. In some embodiments, surface 72 includes a material, such as, for example, a deformable material, such as, for example, silicone or elastomer (e.g., synthetically produced butyl rubber or neoprene or a natural rubber) disposed about passageway 74 to facilitate engagement of cannula 86 with member 42. It is envisioned that all or only a portion of ball 76, collet 78, passageway 74 and/or passageway 90 may have alternate cross section configurations, such as, for example, circular, oval, oblong, triangular, square, rectangular, polygonal, irregular, uniform, non-uniform, offset, staggered, undulating, arcuate, variable and/or tapered, depending upon the requirements of a particular application. In one embodiment, ball can a have silicone lining for friction fit with cannula. In another embodiment, ball can snap onto cannula instead of sliding through hole.

Collet 78 includes an outer surface having an unthreaded first portion 92 and extending from threaded portion 80. Cap 86 includes a first end that includes surface 82 and a second end having an angled inner surface 94 that is free of threads. Surface 82 is configured to engage surface 80 to engage cap 84 with collet 78. As surface 82 engages surface 80, cap 84 is rotated in the direction shown by arrow D or arrow DD such that cap 84 translates relative to collet 78 in the direction shown by arrow E. As cap 84 translates in the direction shown by arrow E, surface 94 engages portion 92 causing inner surface 72 to engage an outer surface of cannula 86. Because surface 94 is angled, rotation of cap 84 in the direction shown by arrow D or arrow DD allows for incremental tightening of surface 72 about cannula 86 such that a restrictive force applied to cannula 86 can be adjusted by altering the amount of rotation of cap 84. When surface 80 is fully threaded with surface 82, cannula 86 becomes fixed relative to collet 78. That is, cap 84 is movable between a first orientation such that surface 82 is spaced apart from surface 80 and cannula 86 is movably disposed within passageway 74 and a second orientation such that surface 82 engages surface 80 and surface 72 engages the outer surface of cannula 86 to fix cannula 86 within passageway 74.

Figure 1:
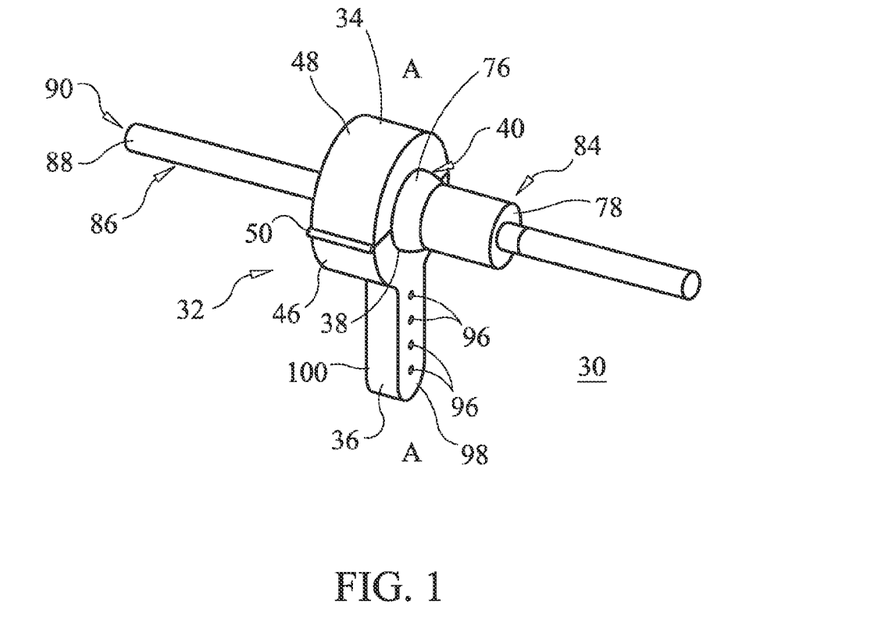
FIG. 1 is a perspective view of one embodiment of components of a system in accordance with the principles of the present disclosure.
Figure 2:
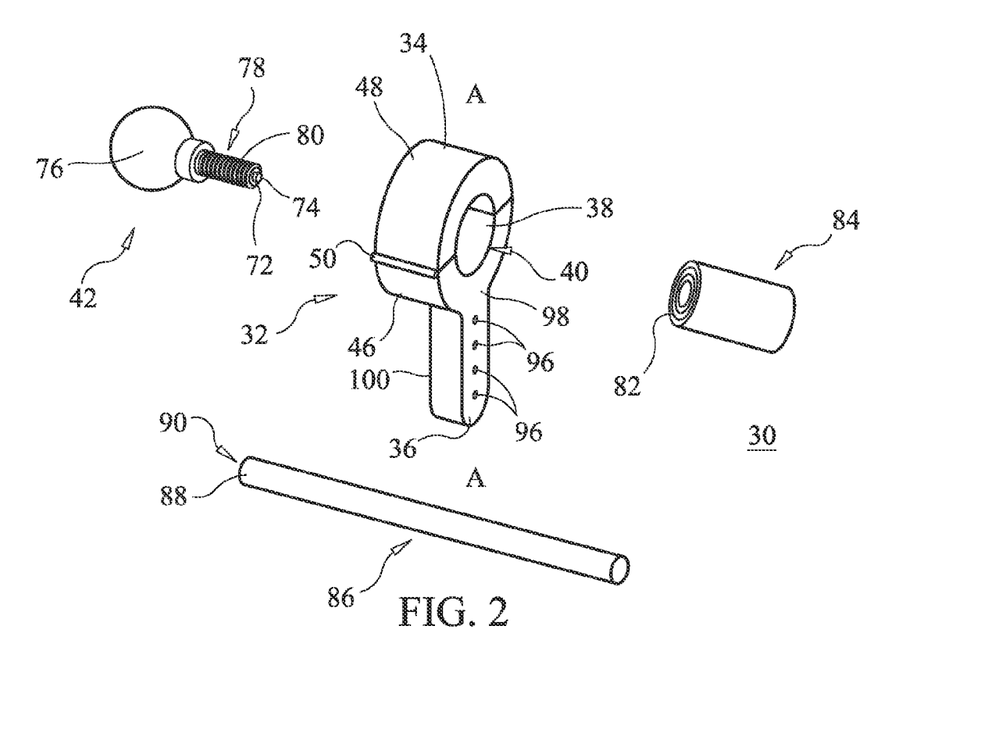
FIG. 2 is a perspective view of the system shown in FIG. 1 with parts separated.
Figure 3:
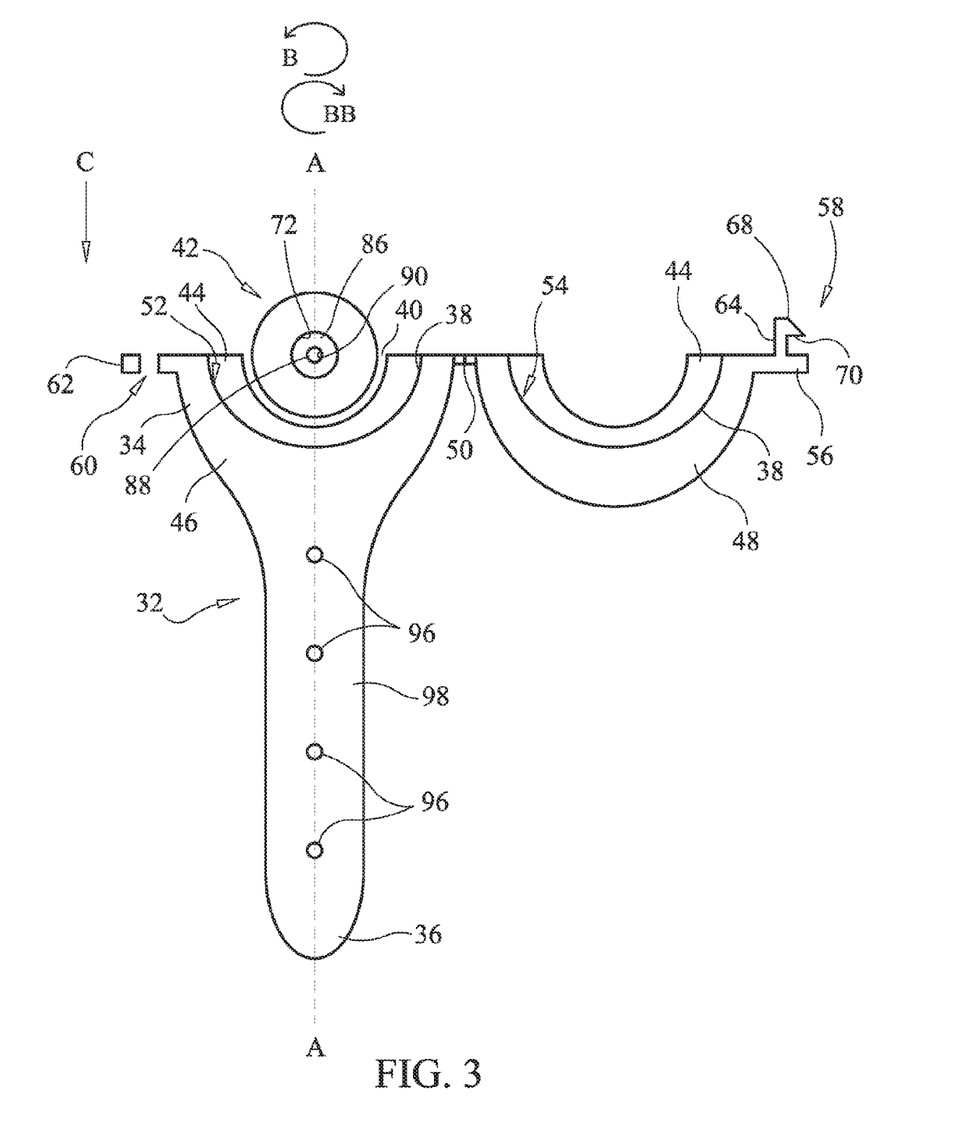
FIG. 3 is a frontal view of components of the system shown in FIG. 1, in part cross section, with a pivoting member in a first orientation.
Figure 4:
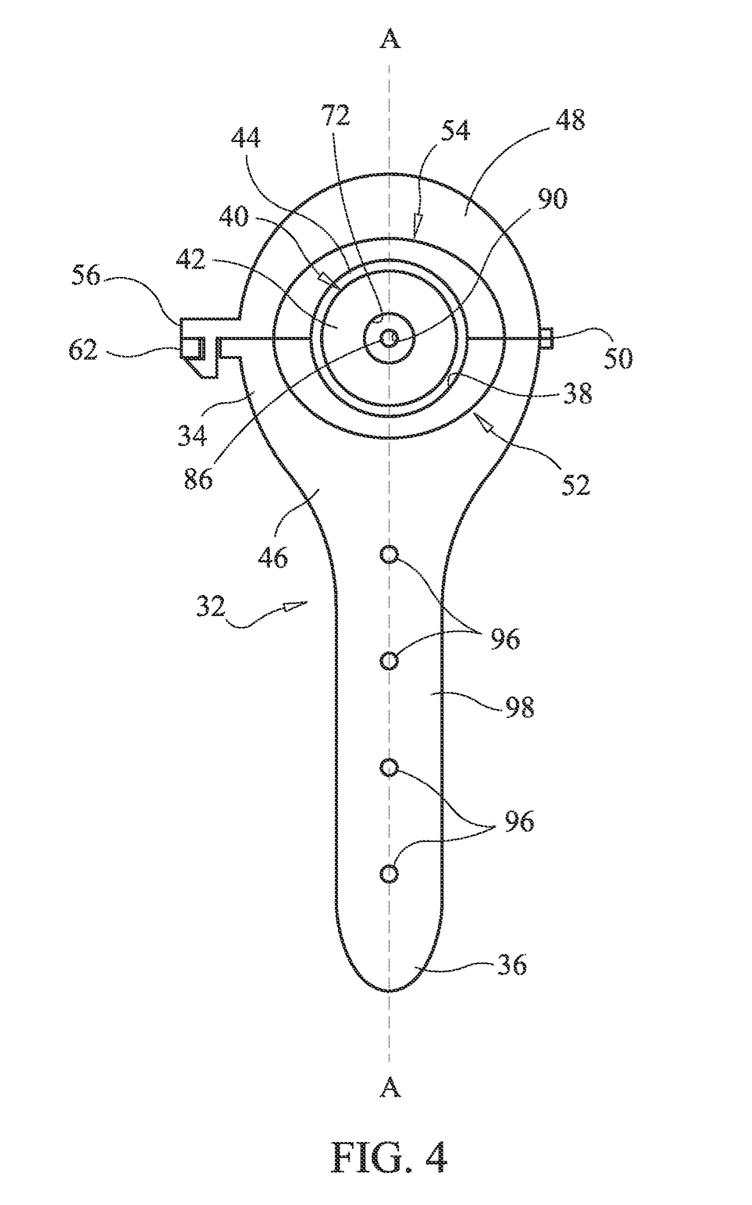
FIG. 4 is a frontal view of components of the system shown in FIG. 1, with the pivoting member in a second orientation.
Figure 5:
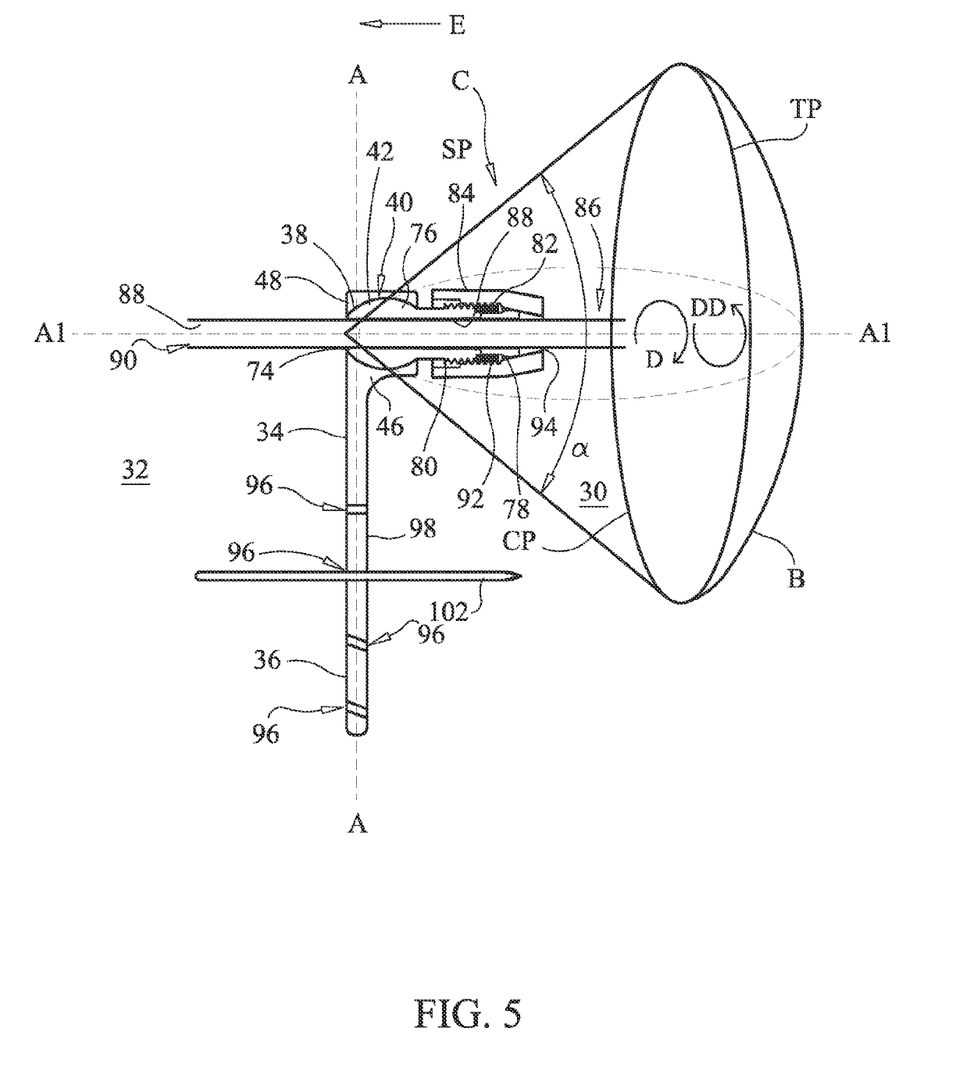
FIG. 5 is a side, cross sectional view of the system shown in FIG. 1.

Member 42 is movable between a first orientation such that portion 48 is spaced apart from portion 46, as shown in FIG. 3, and member 42 is rotatable to a selected trajectory relative to axis A and a second orientation such that portion 48 engages portion 46 and tab 58 is disposed in opening 60 to fix portion 48 relative to portion 46, as shown in FIG. 4, to fix member 42 in the selected trajectory. When member 42 is in the first orientation, passageway 74 is rotatable to a selected angle through and within angular range a relative to axis a in a plurality of planes that lie in a cone configuration C, as shown in FIG. 5. The area and/or volume defined by cone C, which includes the configuration disposed between a transverse axis A1 and a circular base B, is defined by the range of motion of passageway 74 axis A1. The plurality of planes includes a locus of all straight line segments that join axis A1 and base B. For example, passageway 74 is separately rotatable to a selected angle within angular range a in each plane corresponding to a particular straight line segment that lies in cone configuration C. It is contemplated that passageway 74 may rotatable through the individual diameters, chords, section and/or radii of base b and/or other portions of cone C. In one embodiment, passageway 74 is rotatable to a selected angle within angular range a in a sagittal plane (SP), corresponding to a particular plane that lies in cone C. In one embodiment, passageway 74 is rotatable to a selected angle within angular range a in a transverse plane (TP), corresponding to a particular plane that lies in cone C. In one embodiment, passageway 74 is rotatable to a selected angle within angular range a in a coronal plane (CP), corresponding to a particular plane that lies in cone C.

In some embodiments, end 36 includes an aperture 96 extending through surfaces a first surface 98 and an opposite second surface 100. Aperture 96 is configured to receive an engagement device, such as, for example a pin or K-wire 102 configured to fix member 32 relative to the anatomy of a patient. It is envisioned that end 36 may include one or a plurality of apertures 96. Apertures 96 may be holes or slots. It is further envisioned that system 30 may include one or a plurality of pins/K-wires 102, corresponding to the number of apertures 96. In one embodiment, In one embodiment, end 36 includes apertures 96 that all extend perpendicular to axis A. In one embodiment, end 36 includes apertures 96 extending perpendicular to axis A positioned proximally of apertures 96 extending at an acute angle relative to axis A. However, it is contemplated that this configuration may be reversed. That is, the apertures 96 that extend at an acute angle relative to axis A may be positioned proximally of the apertures 96 that extend perpendicular to axis A. It is contemplated that the apertures 96 that extend at an acute angle relative to axis A may alternate with the apertures 96 that extend perpendicular to axis A. It is envisioned that apertures 96 may be disposed through angular ranges in various orientations relative to axis A, such as, for example, transverse or perpendicular and/or other angular orientations such as acute or obtuse, and/or may be offset or staggered. In some embodiments, apertures 96 and/or pins/K-wires 102 may be rough, textured, porous, semi-porous, dimpled and/or polished to facilitate engagement between apertures 96 and pins/K-wires 102.

In assembly, operation and use, system 30 is employed with a surgical procedure, such as, for a correction or treatment of a bone defect, such as, for example, a fracture. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a distal radius or a vertebra. It is envisioned that system 30 may also be used to treat other affected portions of the patient, such as, for example, a calcaneus bone, bones of the feet or hands, bones of the legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a particular surgical application.

Pins/K-wires 102 are positioned within through apertures 96 and are disposed in the anatomy of the patient, such as, for example, tissue, to fix or stabilize member 32 relative to the anatomy of the patient, with cannula 86 positioned within passageway 74. Member 32 is stabilized with pins/K-wires 102.

Surface 82 is aligned with surface 80. Cap 84 is rotated in the direction shown by arrow D or arrow DD such that surface 82 engages surface 80 and cap 84 translates relative to collet 78 in the direction shown by arrow E. Cap 84 is translated in the direction shown by arrow E until surface 94 engages portion 92 causing inner surface 72 to engage the outer surface of cannula 86 such that cannula 86 is fixed relative to member 42. Member 42 is then rotatable to a selected trajectory relative to axis A such that cannula 86 is positioned adjacent the bone disorder. Portion 48 is rotated relative to portion 46 such that portion 48 engages portion 46 and tab 58 is disposed in opening 60 to fix portion 48 relative to portion 46, to fix member 42 in the selected trajectory.

An inflatable bone tamp may then be delivered through cannula 86 to a location adjacent the bone disorder or defect. The inflatable bone tamp may then be expanded to create a cavity or void in the bone by delivering a material, such as, for example, saline, a contrast solution or compressed air into an expandable member of the inflatable bone tamp, such as, for example, a balloon, to move the balloon from an unexpanded configuration to an expanded configuration. As the balloon moves from the unexpanded configuration to the expanded configuration, the balloon creates a void in the bone having the defect or disorder. Member 42 maintains cannula 86 in a stabilized orientation with respect to the body such that a single practitioner can insert the inflatable bone tamp through cannula 86 and operate the inflatable bone tamp in a steady manner. That is, cannula 86 remains at the selected trajectory such that a distal end of cannula 86 is positioned adjacent the bone defect, without the need for a physician or physician's assistant to hold cannula 86.

After the void is formed in the bone, the inflatable bone tamp is removed from cannula 86. Bone filler material or a separate tool configured to deliver bone filler material is then positioned in cannula 86 so as deliver the bone filler material into the void so as to at least partially fill the void and realign fragments of the fracture and/or elevate collapsed bone to its proper height. Member 42 maintains cannula 86 in a stabilized orientation with respect to the body such that a single practitioner can administer the bone filler material in a steady manner. That is, cannula 86 remains at the selected trajectory such that a distal end of cannula 86 is positioned adjacent the bone defect, without the need for a physician or physician's assistant to hold cannula 86. It is envisioned that the bone filler material may include autograft, allograft, demineralized bone matrix, mineral composites, blocks, granules and pellets and bone cement, such as, for example, polymethylmethacrylate (PMMA)-based material (Kyphon HV—R, ActivOs, ActivOs 10, Xpede), calcium phosphate (Skaffold, Norian, Hydroset, KyphOs FS) and calcium sulfate (OsteoSet), as well as other injectables.

In one embodiment, system 30 includes an agent, which may be disposed, packed or layered within, on or about the components and/or surfaces of the components of system 30. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A device for holding a surgical tool comprising:
   a first member extending along a longitudinal axis between a first end and a second end, the first end including a first portion connected to a second portion by a hinge, an inner surface of the first portion and an inner surface of the second portion defining a cavity;
   a pivoting member movably disposed in the cavity including a first inner surface, the first inner surface defining a first passageway, the pivoting member further including a first end comprising a ball and a second end comprising a collet;
   a cap having an inner surface configured to engage an outer surface of the collet; and
   a second member disposed within the first passageway, the second member including a second inner surface, the second inner surface defining a second passageway, the second passageway being configured to include therein one of an inflatable bone tamp, a bone void filler, and a tool adapted to deliver a bone void filler;
   wherein the pivoting member is movable between a first orientation such that the second portion is spaced apart from the pivoting member and the pivoting member is rotatable to a selected trajectory relative to the longitudinal axis and a second orientation such that the second portion engages the pivoting member to fix the second member in the selected trajectory.

2. A device according to claim 1, wherein the cavity is substantially spherical.

3. A device according to claim 1, wherein the outer surface of the collet and the inner surface of the cap are threaded, the threads on the outer surface of the collet being configured to engage the threads on the inner surface of the cap to fix the second member relative to the pivoting member.

4. A device according to claim 1, wherein the outer surface of the collet and the inner surface of the cap are threaded, and wherein the cap is movable between a first orientation such that the threaded inner surface of the cap is spaced apart from the threaded outer surface of the collet and the second member is movably disposed within the passageway and a second orientation such that the threaded inner surface of the cap engages the threaded outer surface of the collet and the second member is fixed within the passageway.

5. A device according to claim 1, wherein the inner surface of the cap includes a threaded first portion and a second portion extending from the first portion that is free of threads, the second portion defining an angled surface.

6. A device according to claim 1, wherein a deformable material is disposed about at least a portion of the cavity, the deformable material being configured to maintain the pivoting member in the second orientation.

7. A device according to claim 1, wherein a material comprising silicone or silicone rubber is disposed about at least a portion of the cavity, the material being configured to maintain the pivoting member in the second orientation.

8. A device according to claim 1, wherein the first portion has an opening and the second portion has a tab configured for disposal in the opening to fix the first portion with the second portion, wherein the tab is spaced apart from the opening when the pivoting member is in the first orientation and the tab is disposed in the opening when the pivoting member is in the second orientation.

9. A device according to claim 8, wherein the opening has a rectangular cross sectional configuration and extends parallel to the longitudinal axis.

10. A device according to claim 8, wherein the tab comprises a resilient material and extends parallel to the longitudinal axis.

11. A device according to claim 8, wherein the tab includes an arm having a uniform width and a catch extending from the arm having a width that is greater than a width of the arm.

12. A device according to claim 11, wherein the catch includes a tapered upper surface and a planar lower surface.

13. A device according to claim 1, wherein the first and second portions are separated by a gap extending transverse to the longitudinal axis.

14. A device according to claim 1, wherein the pivoting member is rotatable in a plurality of planes.

15. A device for performing a surgical procedure comprising:
   a first member extending along a longitudinal axis between a first end and a second end, the first end comprising an inner surface defining a substantially spherical cavity having silicone disposed about at least a portion thereof, the first end of the first member including a first portion connected to a second portion of the first end by a hinge, the first and second portions being separated by a gap extending transverse to the longitudinal axis;
   a pivoting member movably disposed in the cavity, the pivoting member including an inner surface defining a passageway, a first end of the pivoting member comprising a ball and a second end of the pivoting member comprising a collet, the collet having a threaded outer surface;
   a second member disposed within the passageway, the second member including an inner surface defining a second passageway having one of an inflatable bone tamp, a bone void filler and a tool configured to deliver a bone void filler disposed therein; and
   a cap having a threaded inner surface configured to engage the threaded outer surface of the collet, wherein the cap is movable between a first orientation such that the threaded inner surface of the cap is spaced apart from the threaded outer surface of the collet and the second member is movably disposed within the passageway and a second orientation such that the threaded inner surface of the cap engages the threaded outer surface of the collet and the second member is fixed within the passageway, wherein the first end of the first member includes a first portion having an opening and a second portion including a resilient tab configured for disposal in the opening to fix the first portion with the second portion, wherein the pivoting member is movable between a first orientation such that the tab is spaced apart from the opening and the second member is rotatable to a selected trajectory relative to the longitudinal axis through a plurality of planes and a second orientation such that the tab is disposed in the opening to fix the second member in the selected trajectory, and wherein the tab includes an arm, the arm having a substantially uniform width, and a catch extending from the arm, the catch having a width that is greater than a width of the arm.

16. A device according to claim 15, wherein the inner surface of the cap includes a threaded first portion and a second portion extending from the first portion that is free of threads, the second portion defining an angled surface.

17. A device according to claim 15, wherein the catch includes a tapered upper surface and a planar lower surface.

\* \* \* \* \*